United States Patent
Shiomitsu

(10) Patent No.: US 10,300,261 B2
(45) Date of Patent: May 28, 2019

(54) NEEDLE-SHAPED BODY AND METHOD FOR PRODUCING NEEDLE-SHAPED BODY

(71) Applicant: TOPPAN PRINTING CO., LTD., Tokyo (JP)

(72) Inventor: Kazuhiko Shiomitsu, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 0 days.

(21) Appl. No.: 15/842,085

(22) Filed: Dec. 14, 2017

(65) Prior Publication Data

US 2018/0117293 A1 May 3, 2018

Related U.S. Application Data

(63) Continuation of application No. PCT/JP2016/068551, filed on Jun. 22, 2016.

(30) Foreign Application Priority Data

Jun. 23, 2015 (JP) .................................. 2015-125950

(51) Int. Cl.
*B81B 1/00* (2006.01)
*B81C 1/00* (2006.01)
*A61M 37/00* (2006.01)
*B29C 45/14* (2006.01)
*B29C 45/40* (2006.01)
(Continued)

(52) U.S. Cl.
CPC ... *A61M 37/0015* (2013.01); *B29C 45/14336* (2013.01); *B29C 45/40* (2013.01); *B29C 65/4835* (2013.01); *B29C 65/4845* (2013.01);
*B81B 1/00* (2013.01); *B81C 1/00* (2013.01); *A61M 2037/0023* (2013.01);
(Continued)

(58) Field of Classification Search
CPC ....... A61M 2037/0053; B29C 44/1252; B29C 44/18; B29C 44/186
See application file for complete search history.

(56) References Cited

U.S. PATENT DOCUMENTS

2015/0141910 A1* 5/2015 Francis ................. A61L 31/041
604/46

FOREIGN PATENT DOCUMENTS

EP 2 823 850 A1 1/2015
JP 2005-021677 1/2005
(Continued)

OTHER PUBLICATIONS

International Search Report Issued in International Patent Application No. PCT/JP2016/068551 dated Sep. 27, 2016.
(Continued)

*Primary Examiner* — Stella K Yi
(74) *Attorney, Agent, or Firm* — Foley & Lardner LLP

(57) ABSTRACT

A method for producing a needle-shaped body having needles on a first surface of a substrate made of a thermoplastic resin, the method including the steps of: forming the needle-shaped body by filling the thermoplastic resin into a duplication plate having recesses that correspond to shapes of the needles; providing a support member made of a material different from a material for the needle-shaped body on a second surface of the substrate which is opposite to the first surface; and removing the needle-shaped body and the support member which are integrally formed from the duplication plate.

14 Claims, 6 Drawing Sheets

(51) Int. Cl.
*B29C 65/48* (2006.01)
*B29L 31/00* (2006.01)
*B29K 101/12* (2006.01)

(52) U.S. Cl.
CPC ............... *A61M 2037/0046* (2013.01); *A61M 2037/0053* (2013.01); *B29K 2101/12* (2013.01); *B29L 2031/759* (2013.01)

(56) References Cited

FOREIGN PATENT DOCUMENTS

| | | |
|---|---|---|
| JP | 2006-341089 | 12/2006 |
| JP | 2006-345983 | 12/2006 |
| JP | 2014-217520 | 11/2014 |
| WO | WO-2006/075689 A1 | 7/2006 |
| WO | WO-2010/140760 | 12/2010 |
| WO | WO-2013/188884 A1 | 12/2013 |
| WO | WO-2014/196522 | 12/2014 |
| WO | WO-2015/016235 | 2/2015 |

OTHER PUBLICATIONS

European Search Report dated Jun. 7, 2018 in corresponding application No. 16814405.3.

\* cited by examiner

NEEDLE-SHAPED BODY AND METHOD FOR PRODUCING NEEDLE-SHAPED BODY

CROSS-REFERENCE TO RELATED PATENT APPLICATIONS

This application is a continuation application filed under 35 U.S.C. § 111(a) claiming the benefit under 35 U.S.C. §§ 120 and 365(c) of International Application No. PCT/JP2016/068551, filed Jun. 22, 2016, which is based upon and claims the benefit of priority of Japanese Patent Application No. 2015-125950, filed Jun. 23, 2015, the entireties of which are hereby incorporated by reference.

TECHNICAL FIELD

The present invention relates to needle-shaped bodies used for drug administration into the skin and a method for producing the needle-shaped bodies.

BACKGROUND ART

Drug administration by injection has been widely used for injection of a drug such as vaccine into the body. Although injection is a highly safe method for administration, it often causes severe pain since an injection needle is deeply pierced into the body to deliver the drug into the subcutaneous tissue. Further, particularly in developing countries, there are many issues such as infection by reuse of injection needle and needle stick accidents.

Therefore, as an alternative drug administration method to injection, attention has been paid to use of an array of a plurality of needle members of micron order to pierce the skin for direct administration of a drug into the skin. According to this method, it is possible to almost avoid producing pain during piercing into the skin since the length of the needle members is controlled not to reach the nerve cells in the dermis layer. Moreover, a drug can be intradermally administered in a convenient manner without using a special tool for drug administration (see PTLs 1 and 2).

Further, when vaccine is intradermally administered using the needle members, the amount of vaccine used can be reduced compared with subcutaneous injection since antigen presenting cells are abundant in the skin.

The needle member must have a thinness and sharpness sufficient for puncturing the skin and a length sufficient for intradermal drug delivery. Accordingly, the needle member desirably has a diameter of several micrometers to several hundreds of micrometers and a length that penetrates through the stratum corneum which is the outermost layer of the skin but does not reach the nerve fibers, which is specifically several tens of micrometers to several hundreds of micrometers.

Materials for the needle member are required to be harmless to the human body even if the needle member is broken and left in the body. For such materials, biocompatible resins such as medical grade silicone, maltose, polyglycolic acid, polylactic acid, and dextran are regarded as promising materials (see PTL 3).

CITATION LIST

Patent Literature

[PTL 1] JP 2006-345983 A
[PTL 2] JP 2006-341089 A
[PTL 3] JP 2005-21677 A

SUMMARY OF THE INVENTION

Technical Problem

For mass production of a fine structure such as the needle member by using the above resin materials with low cost, a transfer molding process such as injection molding, imprinting or casting is effective. However, in any of the above processes, a mold having an inverted shape of a desired shape is necessary. Accordingly, there is a problem that production of a structure having a high aspect ratio (ratio of the height or depth to a diameter of the structure) requires complicated production steps.

These biocompatible resins are expensive in cost compared with general resin materials, and one of the effective techniques for cost reduction is reducing the amount of use without impairing the function.

Further, by reducing the thickness of a substrate, which is a portion other than the needle, the substrate can flexibly deform in conformity with the irregularities of a target object.

However, for example in producing a needle-shaped body having a thin substrate with approximately 100 µm thickness, a production method may become a matter of consideration.

In particular, when the needle-shaped body is produced by plastic molding, demolding by using a general ejector pin cannot be performed since the substrate does not have a sufficient strength.

Moreover, there is a difficulty in handling after molding.

The present invention has been made in view of the above problem. An object of the invention is to provide a needle-shaped body having a thin substrate and a method for producing the needle-shaped body in a convenient and inexpensive manner.

Solution to Problem

A needle-shaped body according to an aspect of the present invention includes a plurality of needles; and a substrate having a first surface on which the needles are formed and a second surface opposite to the first surface, wherein a height H of each of the needles in a direction perpendicular to the first surface is 50 µm or more and 1000 µm or less, a thickness T1 of the substrate in a direction perpendicular to the first surface is 50 µm or more and 300 µm or less, and an aspect ratio (H/φ), which is a ratio of the height H of the each of the needles to a maximum diameter φ of a connection surface of the first surface to the needles is in a range of 0.7 or more and 10 or less.

A method for producing a needle-shaped body having needles on a first surface of a substrate made of a thermoplastic resin according to an aspect of the present invention, the method includes the steps of: forming the needle-shaped body by filling the thermoplastic resin into a duplication plate having recesses that correspond to shapes of the needles; providing a support member made of a material different from a material for the needle-shaped body on a second surface of the substrate which is opposite to the first surface; and removing the needle-shaped body and the support member which are integrally formed from the duplication plate.

Advantageous Effects of Invention

According to the present invention, a needle-shaped body having a thin substrate can be produced even if the needle-shaped body is made of a thermoplastic resin.

DESCRIPTION OF REPRESENTATIVE EMBODIMENTS

With reference to the drawings, a structure of a needle-shaped body and a method for producing the needle-shaped body according to embodiments of the present invention will be described in detail. Drawings are schematic diagrams of the embodiments for promoting understanding of the embodiments. Although the shapes, dimensions and ratios may be different from those of the actual components, the design can be appropriately changed. It is also to be understood that the examples below are intended to be representative of the present invention. The present invention is not intended to be limited to the embodiments described below.

First Embodiment

Figure 1:
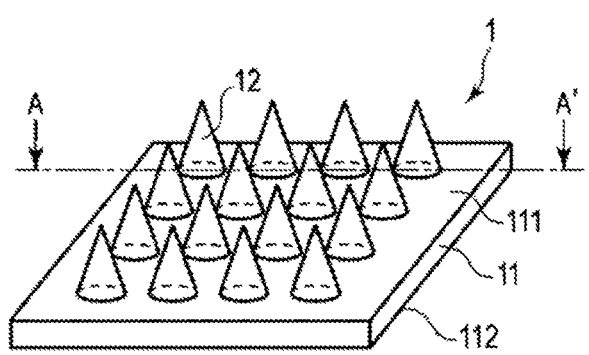
FIG. 1 is a perspective view of a needle-shaped body according to a first embodiment of the present invention.

FIG. 1 is a perspective view of an example of a needle-shaped body 1 of a first embodiment. The needle-shaped body 1 is used for drug administration into the skin. The needle-shaped body 1 is made of a thermoplastic resin.

The needle-shaped body 1 includes a substrate 11 and a plurality of needles 12. The needle-shaped body 1 is, for example, a coating-type microneedle having a drug coated on the needles 12. The substrate 11 includes a first surface (also called a needle forming surface) 111 and a second surface (also called a non-needle forming surface) 112 located opposite to the first surface 111. The first surface 111 and the second surface 112 are flat surfaces parallel to each other. The first surface 111 and the second surface 112 are the same shape and are square. Further, the first surface 111 and the second surface 112 may be a circle or other shapes. In the first embodiment, a direction perpendicular to the first surface 111 and the second surface 112 is referred to as a first direction. A thickness (width in the first direction) of the substrate 11 is as thin as approximately 100 µm, for example. This thickness is merely an example.

The needles 12 are formed on the first surface 111 of the substrate 11. Sixteen needles 12 are formed on the first surface 111 of the substrate 11. Any numbers of needles 12 may be provided. The needles 12 are arranged to extend in the first direction from the first surface 111 of the substrate 11. The needle 12 shown in FIG. 1 has a cone shape. Further, the needle 12 may be a pyramid shape or other shapes. The needles 12 are arranged in a regular grid pattern. The needles 12 may be arranged in other patterns than a regular grid pattern.

Figure 2:
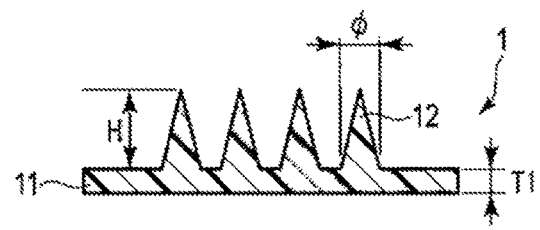
FIG. 2 is a cross-sectional view of the needle-shaped body according to the first embodiment of the present invention.

FIG. 2 is a cross-sectional view of the needle-shaped body 1 taken along the line A-A' shown in FIG. 1. With reference to FIG. 2, exemplary dimensions of the needle-shaped body 1 according to the first embodiment will be described.

The needle 12 has a height H in the first direction. The height H is in the range of 50 µm or more and 1000 µm or less. This range of the height H is required to ensure the needle 12 to pierce or puncture the skin.

The substrate 11 has a thickness T1 in the first direction. The thickness T1 is in the range of 50 µm or more and 300 µm or less. If the thickness T1 of the substrate 11 is less than 50 µm, it may be difficult to cover a surface of the substrate 11 on which the needles 12 are formed. If the thickness T1 of the substrate 11 is more than 300 µm, a support member 5, which will be described later, may be unnecessary in producing the needle-shaped body 1. Therefore, the thickness T1 of the substrate 11 is in the range of 50 µm or more and 300 µm or less.

A connection surface (virtual plane) of the first surface 111 to the needle 12 has a maximum diameter φ. An aspect ratio (H/φ), a ratio of the height H of the needle 12 to the maximum diameter y is in the range of 0.7 or more and 10 or less. This range of the aspect ratio (H/φ) is required to ensure the needle 12 can pierce or puncture the skin.

Figure 3:
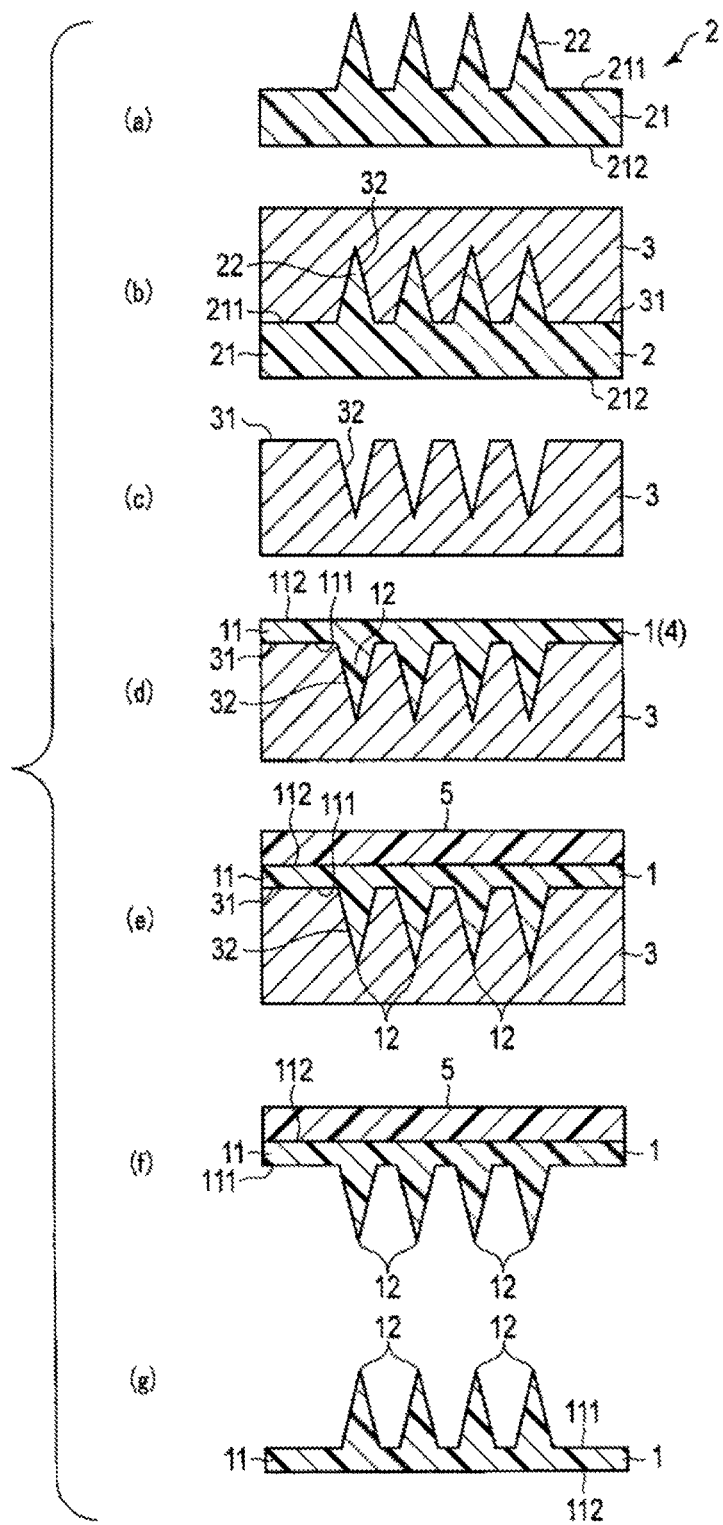
FIG. 3 is a diagram illustrating a method for producing the needle-shaped body according to the first embodiment of the present invention.

FIG. 3 is a diagram illustrating a method for producing the needle-shaped body 1 of the first embodiment. The diagram of the needle-shaped body 1 shown in (g) of FIG. 3 is a cross-sectional view of the needle-shaped body 1 taken along the line A-A' shown in FIG. 1. A specific example of the production method will be described below.

A step shown in (a) of FIG. 3 is a step of preparing a prototype 2 for producing the needle-shaped body 1.

The prototype 2 is used to produce a duplication plate 3 used for mass production of the needle-shaped bodies 1 of the same shape. The prototype 2 includes a substrate 21 and a plurality of needles 22.

The substrate 21 includes a first surface 211 and a second surface 212 located opposite to the first surface 211. The first surface 211 and the second surface 212 are flat surfaces parallel to each other. The first surface 211 and the second surface 212 are the same shape. The shapes of the first surface 211 and the second surface 212 correspond to the shapes of the first surface 111 and the second surface 112 of the needle-shaped body 1, respectively. The thickness of the substrate 21 is larger than the thickness of the substrate 11 of the needle-shaped body 1.

The needles 22 are formed on the first surface 211 of the substrate 21. The needles 22 are arranged to extend in a direction perpendicular to the first surface 211 of the substrate 21. The number, shape, arrangement, and the like of the needles 22 correspond to the number, shape, arrangement, and the like of the needles 12 of the needle-shaped body 1 to be produced. As described above, the prototype 2 corresponds to the shape of the needle-shaped body 1 with the thickness of the substrate 11 increased. For example, the prototype 2 is made of silicon. However, other materials may be used for the prototype 2.

A step shown in (b) of FIG. 3 is a step of producing the duplication plate 3. The duplication plate 3 is produced by applying the material for forming the duplication plate 3 onto the prototype 2. The duplication plate 3 has an inverted shape of the prototype 2 or the needle-shaped body 1 to be produced.

That is, the duplication plate 3 includes a first surface 31 having the same shape as that of the first surface 211 of the prototype 2 or the first surface 111 of the needle-shaped body 1 to be produced. The first surface 31 is a flat surface. The duplication plate 3 has a plurality of recesses 32 on the first surface 31. The recesses 32 are formed to extend in a direction perpendicular to the first surface 31. The shape of the recess 32 corresponds to that of the needle 22 of the prototype 2 or the needle 12 of the needle-shaped body 1 to be produced. For example, the duplication plate 3 is made of a metal such as nickel (Ni) or a resin such as silicone rubber. However, other materials may be used for the duplication plate 3.

A step shown in (c) of FIG. 3 is a step of removing the prototype 2 from the duplication plate 3. The prototype 2 can be removed from the duplication plate 3, for example, by using a hot alkali solution. However, other techniques may also be used. According to the step of removing the prototype 2, the duplication plate 3, which serves as a mold of the needle-shaped body 1 to be produced, can be prepared. In (c) of FIG. 3, the duplication plate 3 is illustrated to be inverted from (b) of FIG. 3.

A step shown in (d) of FIG. 3 is a step of filling a thermoplastic resin 4 into the duplication plate 3 to form the needle-shaped body 1. An example of this step will be described. First, the thermoplastic resin 4 is placed on the first surface 31 of the duplication plate 3. Then, the thermoplastic resin 4 placed on the first surface 31 is melted. Then, the thermoplastic resin 4 is pressed into the recesses 32 of the duplication plate 3 under pressure so that the thermoplastic resin 4 is filled into the recesses 32. The thermoplastic resin 4 is shaped by the duplication plate 3. The amount of the thermoplastic resin 4 to be filled into the duplication plate 3 can be adjusted so that the substrate 11 of the needle-shaped body 1 to be finally produced has a predetermined thickness. The supply amount of the thermoplastic resin 4 to the duplication plate 3 can be limited, or the excess of the thermoplastic resin 4 can be reused by placing outside the frame of the duplication plate 3. Accordingly, a substantial increase in the production cost of the substrate 11 can be prevented while maintaining a predetermined thickness of the substrate 11. The thermoplastic resin 4 produced by the duplication plate 3 constitutes the needle-shaped body 1.

Next, materials for the thermoplastic resin 4 will be described.

The needle-shaped body 1 of the present invention pierces or punctures the skin by the needles 12. For this reason, the thermoplastic resin 4 is biocompatible. The needle-shaped body 1 made of a biocompatible thermoplastic resin can be safely used with the living body.

For the thermoplastic resin 4, for example, polyglycolic acid (hereinafter, referred to as PGA), polylactic acid, polyethylene, polypropylene, polystyrene, polyamide, polycarbonate, cyclic polyolefin, polycaprolactone, acrylic resin, nylon resin, urethane resin, aromatic polyether ketone, polyethylene terephthalate, polyethylene naphthalate, epoxy resin or the like can be used. Among others, biocompatible medical grade resin such as biocompatible polyglycolic acid (hereinafter, referred to as PGA) and polylactic acid can be preferably used. Further, the thermoplastic resin 4 may be other resins than those described above as long as they have thermoplasticity.

The thermoplastic resin 4 may be a material having a low melting point. As described later, the needle-shaped body 1 may be melted during placement of the support member 5 on the second surface 112 of the needle-shaped body 1. The support member 5 is placed on the second surface 112 of the melted needle-shaped body 1 and is pressurized. As a result, the support member 5 is closely attached to the needle-shaped body 1. For this reason, the melting point of the material that constitutes the support member 5 is preferably higher than the melting point of the thermoplastic resin 4. As the melting point of the thermoplastic resin 4 becomes lower, the material for forming the support member 5 can be selected from a wide variety of materials.

A step shown in (e) of FIG. 3 is a step of placing the support member 5 on the second surface 112 of the needle-shaped body 1. According to this step, the support member 5 is adhered to the second surface 112 of the needle-shaped body 1. The support member 5 can reinforce the substrate 11 since it is laminated on the substrate 11 of the needle-shaped body 1. The support member 5 contributes to removing the needle-shaped body 1 from the duplication plate 3.

Materials for forming the support member 5 will be described. The support member 5 is made of a material different from the material forming the needle-shaped body 1. One of the reasons for that is that the support member 5 is finally removed from the needle-shaped body 1. The material for forming the support member 5 is not necessarily as expensive a material as the material forming the needle-shaped body 1, and may be an inexpensive material.

The support member 5 may be made of a material soluble in a specific solvent. The material soluble in a specific solvent is a material that dissolves selectively in the specific solvent compared with the material forming the needle-shaped body 1. The material soluble in a specific solvent is, for example, a water-soluble material. The water-soluble material can use water, which is inexpensive and safe, as a solvent. The water-soluble material may be, for example, polyvinyl alcohol (hereinafter, referred to as PVA), cellulose and a cellulose derivative, chitosan and a chitosan derivative, polyacrylic acid polymer, polyacrylic amide (PAM), or polyethylene oxide. The material soluble in a specific solvent used for the support member may be other resins than those described above.

The support member 5 may be made of a material having adhesiveness that varies in response to external stimulation. The external stimulation is, for example, ultraviolet light (UV), an electron beam (EB), infrared light or heat, but not limited thereto. An example of the material having adhesiveness that varies in response to an ultraviolet light is a material used for a dicing tape. An example of the material having adhesiveness that varies in response to an infrared light or heat is a heat-sensitive adhesive sheet. The heat-sensitive adhesive sheets may be a cool off type or a warm off type.

A step shown in (e) of FIG. 3 is a step of placing the support member 5, some examples of which will be described below.

First, the thermoplastic resin 4 that constitutes the second surface 112 of the substrate 11 of the needle-shaped body 1 is melted. Then, the support member 5 is placed on the second surface 112 of the needle-shaped body 1. Then, pressure is applied to the support member 5. The support member 5 is closely attached to the needle-shaped body 1, and thus adhered to the needle-shaped body 1.

An example of the step shown in (e) of FIG. 3, in which the material has adhesiveness that varies in response to external stimulation will be described. As shown in (e) of FIG. 3, the step of placing the support member 5 on the second surface 112 of the substrate 11 is a step of adhering the support member 5 made of a material having adhesiveness that varies in response to external stimulation to the second surface 112 of the substrate 11. In this step, the support member 5 is first placed on the second surface 112 of the needle-shaped body 1. Then, external stimulation is applied to the support member 5. Accordingly, the adhesiveness of the support member 5 varies. For example, the support member 5 is softened. By virtue of the adhesiveness of the support member 5, the support member 5 is closely attached to the needle-shaped body 1, and thus adhered to the needle-shaped body 1.

Further, rather than the material of the support member 5 having such adhesiveness, an adhesive having adhesiveness that varies in response to external stimulation may be used. In this case, the step of placing the support member 5 on the second surface 112 of the substrate 11 shown in (e) of FIG. 3 is a step of adhering the support member 5 to the second surface 112 of the substrate 11 by using an adhesive having adhesiveness that varies in response to external stimulation.

In addition, the support member 5 may be formed concurrently with processing the thermoplastic resin 4 into the needle-shaped body 1. For example, the thermoplastic resin 4 is placed on the first surface 31 of the duplication plate 3 in the step shown in (d) of FIG. 3. Then, the support member 5 is placed on the thermoplastic resin 4, and pressure is applied to the support member 5 so that the recess 32 is filled with the thermoplastic resin 4. Accordingly, the needle-shaped body 1 is formed while the support member 5 is disposed on the second surface 112 of the needle-shaped body 1. This molding technique can reduce the number of steps for producing the needle-shaped body 1.

A step shown in (f) of FIG. 3 is a step of removing the needle-shaped body 1 and the support member 5 which are integrally formed from the duplication plate 3. According to this step, the needle-shaped body 1 having the integrally formed support member 5 can be obtained. An example of demolding technique used in this step is suctioning the surface of the support member 5 opposite from the surface that is in contact with the second surface 112 of the needle-shaped body 1 by vacuuming. Another example of a demolding technique is pushing out the needle-shaped body 1 and the support member 5 which are integrally formed from the duplication plate 3 by using an ejector pin. Other demolding techniques than those described above may also be used.

Taking the support member 5 and the needle-shaped body 1 as a unit, a sum of the thickness of the support member 5 and the thickness of the substrate 11 of the needle-shaped body 1 is larger than the thickness of the substrate 11 of the needle-shaped body 1 alone. The substrate 11 of the needle-shaped body 1 having the integrally formed support member 5 has a strength larger than that of the substrate 11 of the needle-shaped body 1 alone. Accordingly, the needle-shaped body 1 having the integrally formed support member 5 can be demolded from the duplication plate 3 with ease. Moreover, the substrate 11 of the needle-shaped body 1 does not suffer damage due to demolding. Here, as a comparative example, demolding of the needle-shaped body 1 alone will be described. Assume that the thickness of the substrate 11 of the needle-shaped body 1 is approximately 100 µm. Since the substrate 11 does not have sufficient strength, the needle-shaped body 1 cannot be demolded even with use of an ejector pin. If the needle-shaped body 1 was demolded, there would be a risk of damage to the needle-shaped body 1.

A step shown in (g) of FIG. 3 is a step of removing the support member 5 from the needle-shaped body 1. Some examples of this step will be described.

An example of the step shown in (g) of FIG. 3, in which the support member 5 is made of a material soluble in a specific solvent will be described. The step of removing the support member 5 from the needle-shaped body 1 shown in (g) of FIG. 3 is a step of removing the support member 5 from the needle-shaped body 1 by using a solvent in which the material constituting the support member 5 is soluble. In this step, the needle-shaped body 1 having the integrally formed support member 5 is immersed in a specific solvent. The specific solvent is a solvent in which the material constituting the support member 5 is soluble. The support member 5 dissolves in the specific solvent. Using the specific solvent promotes removal of the support member 5 from the needle-shaped body 1 without applying an external force to the support member 5. As a result, the needle-shaped body 1 made up of solely the thermoplastic resin 4 can be obtained.

An example of the step shown in (g) of FIG. 3, in which the material of the support member 5 has adhesiveness that varies in response to external stimulation will be described. In this step, external stimulation is applied to the support member 5. The external stimulation is applied to the surface of the support member 5 opposite from the surface that is in contact with the second surface 112 of the needle-shaped body 1. The adhesiveness of the support member 5 varies by the external stimulation. As the adhesiveness of the support member 5 decreases, the adhesiveness between the support member 5 and the needle-shaped body 1 decreases. As a result, the support member 5 can be removed from the needle-shaped body 1. Applying external stimulation to the support member 5 promotes removal of the support member 5 from the needle-shaped body 1 without applying a strong external force to the support member 5. As a result, the needle-shaped body 1 made up of solely the thermoplastic resin 4 can be obtained.

An example of the step shown in (g) of FIG. 3, in which the support member 5 is adhered to the needle-shaped body 1 by using an adhesive having adhesiveness that varies in response to external stimulation will be described. The step of removing the support member 5 from the needle-shaped body 1 shown in (g) of FIG. 3 is a step of removing the support member 5 from the needle-shaped body 1 by applying external stimulation. In this step, external stimulation is applied to the adhesive. The external stimulation is applied to the surface of the support member 5 opposite from the surface that is in contact with the second surface 112 of the needle-shaped body 1. The adhesiveness of the adhesive varies by the external stimulation. As the adhesiveness of the adhesive decreases, the adhesiveness between the support member 5 and the needle-shaped body 1 decreases. As a result, the support member 5 can be removed from the needle-shaped body 1. Applying external stimulation to the adhesive promotes removal of the support member 5 from the needle-shaped body 1 without applying a strong external force to the support member 5. As a result, the needle-shaped body 1 made up of solely the thermoplastic resin 4 can be obtained.

Further, in the step shown in (g) of FIG. 3, a release agent can be used to remove the support member 5 from the needle-shaped body 1. Using the release agent promotes removal of the support member 5 from the needle-shaped body 1 without applying a strong external force to the support member 5. As a result, the needle-shaped body 1 made up of solely the thermoplastic resin 4 can be obtained.

According to the method of producing the needle-shaped body 1 of the first embodiment, the needle-shaped body 1 having the thin substrate 11 can be easily produced even if the needle-shaped body 1 is formed of the thermoplastic resin 4. Further, although it is necessary to use an expensive biocompatible medical grade thermoplastic resin 4 since the needle-shaped body 1 pierces or punctures the skin, the amount of the thermoplastic resin 4 used is reduced by forming the thin substrate 11 of the needle-shaped body 1. Further, the production cost can be reduced since the needle-shaped body 1 is formed in a size that can be easily removed from the duplication plate 3.

Moreover, since the needle-shaped body 1 having the thin substrate 11 has flexibility after removing the support member 5, it can be bent in conformity with the skin. Accordingly, the needle-shaped body 1 having the thin substrate 11 by removing the support member 5 can pierce and puncture the skin by the needles 12 to a sufficient extent.

Second Embodiment

A second embodiment will be described below. Parts that may be the same as those of the first embodiment are denoted by the same reference numbers, and the description thereof will be omitted.

Figure 4:
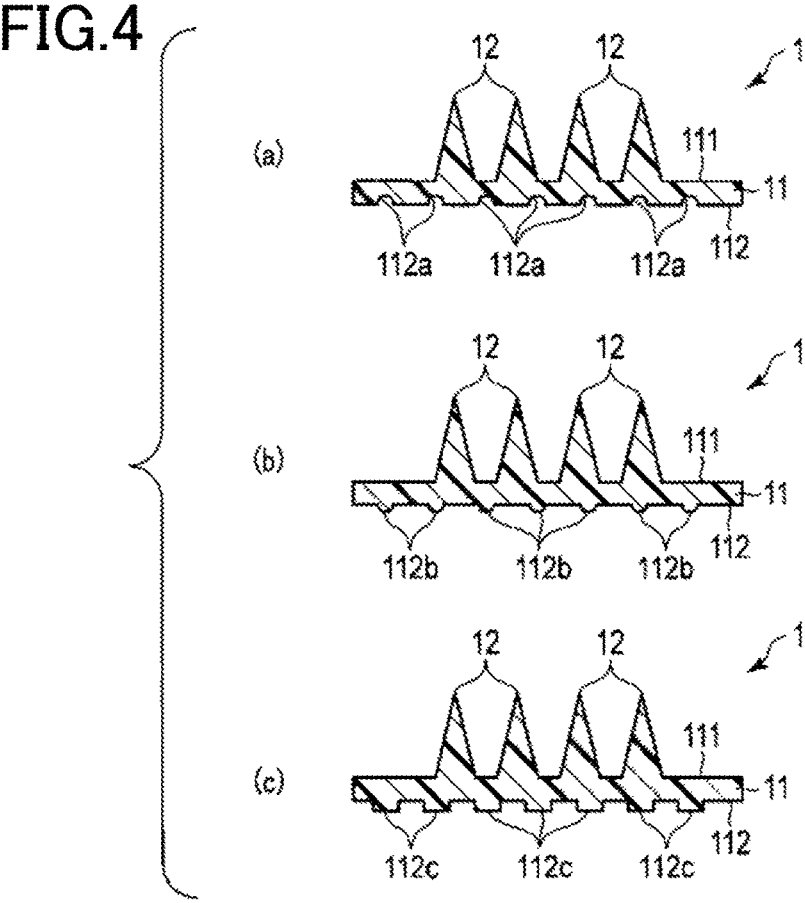
FIG. 4 is a diagram illustrating a structure of the needle-shaped body according to a second embodiment of the present invention.

FIG. 4 is a diagram illustrating a structure of the needle-shaped body 1 according to a second embodiment. FIG. 4 is a cross-sectional view of the needle-shaped body 1 taken along the line A-A' shown in FIG. 1.

The diagram shown in (a) of FIG. 4 is an example of the needle-shaped body 1 according to the second embodiment. A plurality of recesses (also called dimple structures) 112a are formed on the second surface 112 of the needle-shaped body 1. The recess 112a has a hemisphere shape. Further, the recess 112a may be a rectangular shape or other shapes. The recesses 112a may be arranged in a regular grid pattern or other patterns than a regular grid pattern. The recesses 112a are transferred by the support member 5 in the step shown in (e) of FIG. 3. Projections that correspond to the recesses 112a are formed on the surface of the support member 5 that is in contact with the second surface 112 of the needle-shaped body 1. The recesses 112a are formed by transferring the shapes corresponding to the projections formed on the surface of the support member 5 that is in contact with the second surface 112 of the needle-shaped body 1.

The diagram shown in (b) of FIG. 4 is an example of the needle-shaped body 1 according to the second embodiment. A plurality of projections (also called embossed structures) 112b are formed on the second surface 112 of the needle-shaped body 1. The projection 112b has a hemisphere shape. Further, the projection 112b may be other shapes. The projections 112b may be arranged in a regular grid pattern or other patterns than a regular grid pattern. The projections 112b are transferred by the support member 5 in the step shown in (e) of FIG. 3. Recesses that correspond to the projections 112b are formed on the surface of the support member 5 that is in contact with the second surface 112 of the needle-shaped body 1. The projections 112b are formed by transferring the shapes corresponding to the recesses formed on the surface of the support member 5 that is in contact with the second surface 112 of the needle-shaped body 1.

The diagram shown in (c) of FIG. 4 is an example of the needle-shaped body 1 according to the second embodiment. A plurality of projections (also called embossed structures) 112c are formed on the second surface 112 of the needle-shaped body 1. The projection 112c has a rectangular shape. Further, the projection 112c may be other shapes. The projections 112c may be arranged in a regular grid pattern or other patterns than a regular grid pattern. The projections 112c are transferred by the support member 5 in the step shown in (e) of FIG. 3. Recesses that correspond to the projections 112c are formed on the surface of the support member 5 that is in contact with the second surface 112 of the needle-shaped body 1. The projections 112c are formed by transferring the shapes corresponding to the recesses formed on the surface of the support member 5 that is in contact with the second surface 112 of the needle-shaped body 1.

Moreover, in addition to the example shown in FIG. 4, recesses or projections such as a pear-skin finish, or combination thereof may be provided on the second surface 112 of the needle-shaped body 1.

By providing the contact surfaces of the needle-shaped body 1 and the support member 5 formed as described above, the needle-shaped body 1 and the support member 5 engage with each other in the step shown in (e) of FIG. 3. For example, the recesses 112a formed on the second surface 112 of the needle-shaped body 1 engage the projections formed on the support member 5 for producing the recesses 112a. The projections 112b or the projections 112c formed on the second surface 112 of the needle-shaped body 1 engage the recesses formed on the support member 5 for producing the projections 112b or the projections 112c.

In general, it is difficult to adhere the flat surfaces of two objects made of different materials. With the aforementioned configuration in which the needle-shaped body 1 and the support member 5 engage each other, the support member 5 and the needle-shaped body 1 can be more reliably adhered to each other.

According to the second embodiment, the support member 5 and the needle-shaped body 1 can be more reliably adhered to each other in the step of placing the support member 5 on the second surface 112 of the needle-shaped body 1. In the steps such as removing the needle-shaped body 1 and the support member 5 which are integrally formed from the duplication plate 3, the needle-shaped body 1 having the integrally formed support member 5 can be easily handled.

Further, in addition to the recesses 112a, the projections 112b or the projections 112c, a structure corresponding to the surface structure of the support member 5 may be provided on the second surface 112 of the needle-shaped body 1. For example, a lot number or a product number may be formed on the surface of the support member 5 that is in contact with the second surface 112 of the needle-shaped body 1. A structure that corresponds to the surface structure of the support member 5 is transferred to the second surface 112 of the needle-shaped body 1.

Third Embodiment

A third embodiment will be described below. Parts that may be the same as those of the first embodiment or the second embodiment are denoted by the same reference numbers, and the description thereof will be omitted.

Figure 5:
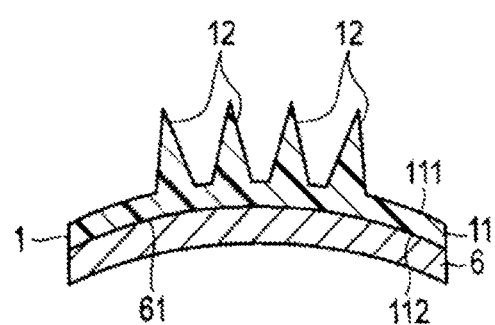
FIG. 5 is a diagram illustrating a structure of the needle-shaped body according to a third embodiment of the present invention.

FIG. 5 is a diagram illustrating a structure of the needle-shaped body 1 according to the third embodiment.

A reinforcement layer 6 has a convex curved surface 61 which is curved at a predetermined curvature. The reinforcement layer 6 is made of a metal, for example, but may be made of other materials. The second surface 112 of the needle-shaped body 1 is adhered to the convex curved surface 61 of the reinforcement layer 6. The second surface 112 of the needle-shaped body 1 is adhered to the curved surface 61, for example, by using an adhesive. The needle-shaped body 1 has the substrate 11 curved into a convex shape along the shape of the reinforcement layer 6.

The substrate 11 can be curved since the needle-shaped body 1 has the thin substrate 11 as described in the first embodiment. The substrate 11 can be curved without causing damage. As a comparative example, assume that the needle-shaped body 1 has the substrate 11 with the thickness of approximately 1000 µm. The substrate 11 with such a thickness cannot be flexibly curved. If this substrate 11 is curved, the substrate 11 is damaged.

Further, the method of producing the needle-shaped body 1 described in the first embodiment may also include a step of adhering the second surface 112 of the substrate 11, with the support member 5 removed, to the convex curved surface 61 of the reinforcement layer 6.

According to the third embodiment, the needle-shaped body 1 in the shape that can be readily pierced into the skin compared with the needle-shaped body 1 having a plate-shaped substrate 11 can be provided.

Fourth Embodiment

A fourth embodiment will be described below. Parts that may be the same as those of the first embodiment, the second embodiment or the third embodiment are denoted by the same reference numbers, and the description thereof will be omitted.

Figure 6:
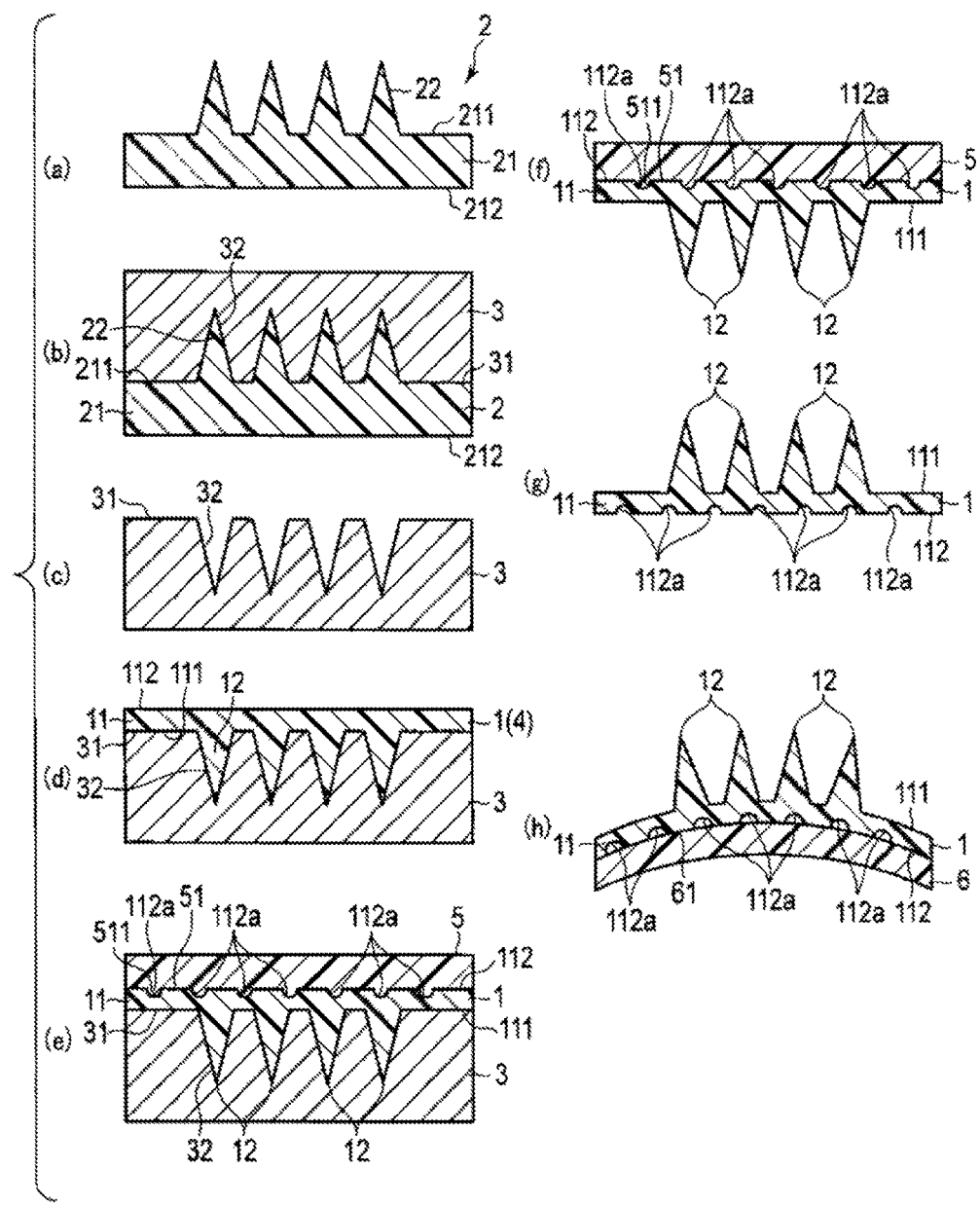
FIG. 6 is a diagram illustrating a method for producing the needle-shaped body according to a fourth embodiment of the present invention.

FIG. 6 is a diagram illustrating a method for producing the needle-shaped body of the fourth embodiment. The diagram shown in (g) of FIG. 6 is a cross-sectional view of the needle-shaped body 1 taken along the line A-A' shown in FIG. 1. A specific example of the production method will be described below. FIG. 6 illustrates a method for producing the needle-shaped body 1 having the recesses 112a which is shown in (a) of FIG. 4 in conjunction with the second embodiment. Further, the method for producing the needle-shaped body 1 having the projections 112b which is shown in (b) of FIG. 4 may be the same as the production method described below, and the description thereof will be omitted. Similarly, the method for producing the needle-shaped body 1 having the projections 112c which is shown in (c) of FIG. 4 may be the same as the production method described below, and the description thereof will be omitted.

Steps shown in (a) to (d) of FIG. 6 may be the same as the steps described above with reference to (a) to (d) of FIG. 3, and the description thereof will be omitted.

The step shown in (e) of FIG. 6 is the same as the step described above with reference to (e) of FIG. 3, except that the support member 5 has a shape different from that of the first embodiment. Here, points different from the first embodiment will be described.

In the fourth embodiment, a plurality of projections (also called embossed structures) 511 are formed on a surface 51 of the support member 5 that is in contact with the second surface 112 of the needle-shaped body 1. In the step shown in (e) of FIG. 6, when the support member 5 is placed on the second surface 112 of the needle-shaped body 1, the shapes which correspond to the projections 511 are transferred to the second surface 112 of the needle-shaped body 1. The recesses 112a having the shapes which correspond to the projections 511 are formed on the second surface 112 of the needle-shaped body 1. The recesses 112a formed on the second surface 112 of the needle-shaped body 1 engage the projections 511 formed on the support member 5. As a result, the support member 5 and the needle-shaped body 1 are more reliably adhered to each other.

A step shown in (f) of FIG. 6 may be the same as the step described above with reference to (f) of FIG. 3, and the description thereof will be omitted. Further, since the support member 5 and the needle-shaped body 1 are reliably adhered to each other as described above, the needle-shaped body 1 having the integrally formed support member 5 can be easily demolded.

A step shown in (g) of FIG. 6 is the same as the step described above with reference to (g) of FIG. 3, and the description thereof will be omitted. According to this step, the needle-shaped body 1 having the recesses 112a made up of solely the thermoplastic resin 4 can be obtained.

A step shown in (h) of FIG. 6 is a step of adhering the second surface 112 of the substrate 11, with the support member 5 removed, to the convex curved surface 61 of the reinforcement layer 6. In this step, for example, the second surface 112 of the needle-shaped body 1 is adhered to the curved surface 61 by using an adhesive. According to this step, the needle-shaped body 1 having the substrate 11 curved into a convex shape along the shape of the reinforcement layer 6 can be obtained.

Further, the method of producing the needle-shaped body 1 according to the fourth embodiment may not necessarily include the step shown in (h) of FIG. 6.

According to the fourth embodiment, the same effects as those described in the first to third embodiments can be obtained.

Fifth Embodiment

A fifth embodiment will be described below. Parts that may be the same as those of the first to fourth embodiments are denoted by the same reference numbers, and the description thereof will be omitted.

Figure 7:
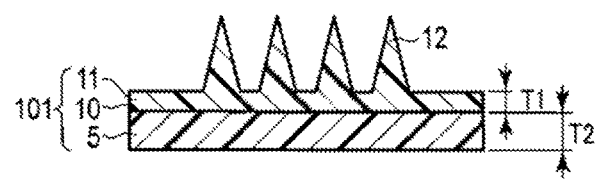
FIG. 7 is a cross-sectional view of the needle-shaped body according to a fifth embodiment of the present invention.

FIG. 7 is a cross-sectional view of a needle-shaped body 101 according to the fifth embodiment. The needle-shaped body 101 includes a needle-shaped body main body 10 and the support member 5. The needle-shaped body main body 10 includes the substrate 11 and a plurality of needles 12. The needle-shaped body main body 10 corresponds to the needle-shaped body 1 described in the first embodiment.

The support member 5 is disposed on the second surface 112 of the substrate 11. Further, the material for forming the support member 5 is not limited to the materials described in the first embodiment. The support member 5 may be made of a general resin film (sheet).

Examples of the resin film for forming the support member 5 include polyglycolic acid (hereinafter, referred to as PGA), polylactic acid, polyethylene, polypropylene, polystyrene, polyamide, polycarbonate, cyclic polyolefin, polycaprolactone, acrylic resin, urethane resin, aromatic polyether ketone, nylon resin, polyethylene terephthalate, polyethylene naphthalate, and resin films made of a thermoplastic resin such as epoxy resin. A non-biocompatible thermoplastic resin may be used as the resin film for forming the support member. Further, the resin film used for the support member may be other resins than those described above.

For example, the thermoplastic resin 4 used for the needle-shaped body 1 and the thermoplastic resin used for the support member 5 may be the same material. The thermoplastic resin 4 used for the needle-shaped body 1 may be an expensive biocompatible resin, and the thermoplastic resin used for the support member 5 may be inexpensive general grade resin.

The support member 5 has a thickness T2 in the first direction. A sum of the thickness T1 of the substrate 11 and the thickness T2 of the support member 5 is in the range of 400 μm or more and 1500 μm or less. When the sum of T1 and T2 is less than 400 μm, easy removal of the needle-shaped body 1 from the duplication plate in production of the needle-shaped body 1 may be difficult. When the sum of T1 and T2 is more than 1500 μm, the production cost increases. Therefore, the sum of T1 and T2 is preferably in the range of 400 μm or more and 1500 μm or less.

Figure 8:
FIG. 8 is a cross-sectional view of a modified example of the needle-shaped body according to a fifth embodiment of the present invention.

FIG. 8 is a cross-sectional view of a modified example of the needle-shaped body 101 according to the fifth embodiment.

The needle-shaped body 101 shown in FIG. 8 includes an adhesive layer 7 between the needle-shaped body main body 10 and the support member 5.

The material for the adhesive layer 7 is not limited as long as the adhesive layer 7 can adhere the needle-shaped body main body 10 to the support member 5.

Next, a method for producing the needle-shaped body 101 will be described.

Figure 9:
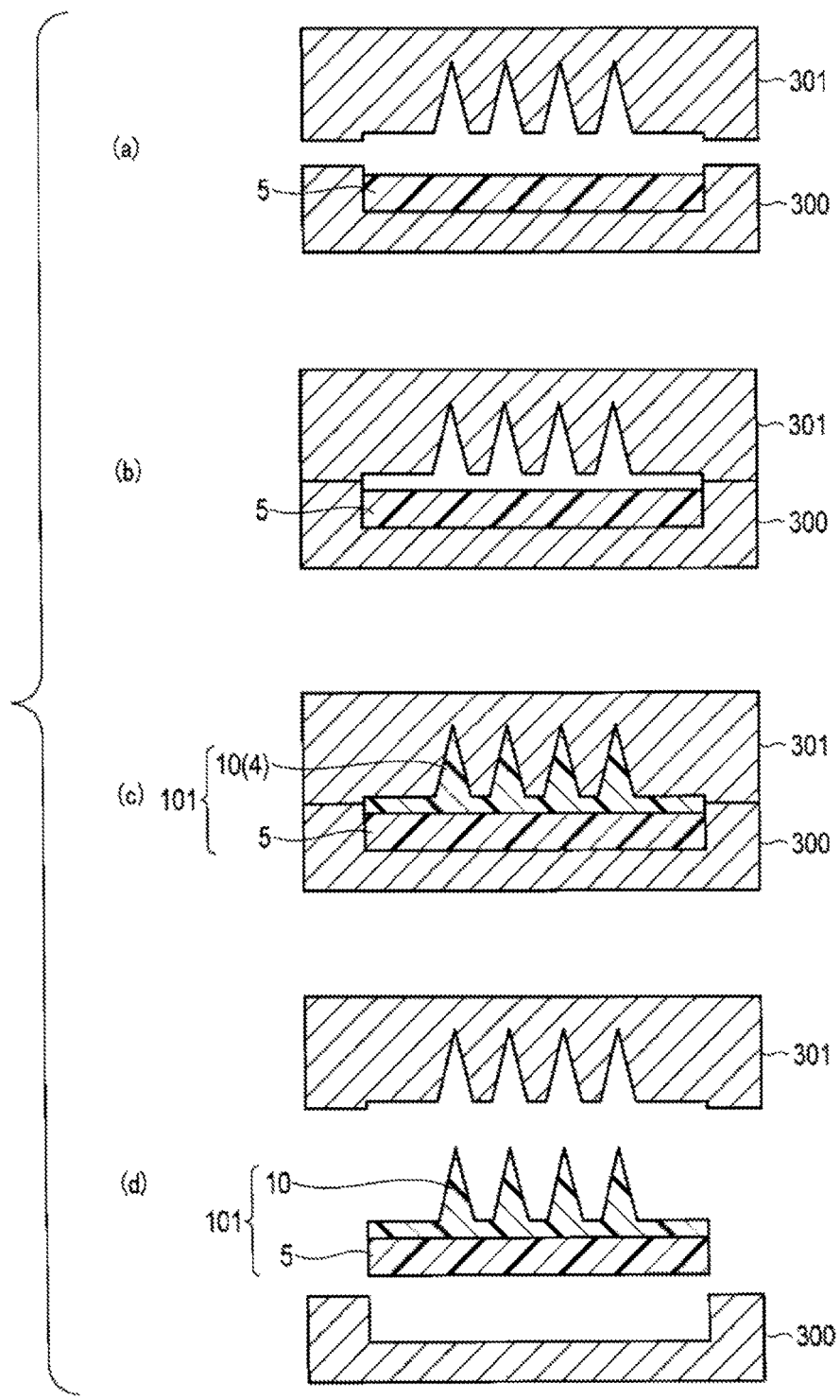
FIG. 9 is a diagram illustrating a method for producing the needle-shaped body according to the fifth embodiment of the present invention.

FIG. 9 is a diagram illustrating an example of the method for producing the needle-shaped body 101. The method shown in FIG. 9 uses injection molding (film insert molding).

A step shown in (a) of FIG. 9 is a step of placing the support member 5 in a first duplication plate 300. The first duplication plate 300 has an inverted shape of the support member 5 of the needle-shaped body 101 to be produced. The first duplication plate 300 is also called an intaglio plate or a mold.

A step shown in (b) of FIG. 9 is a step of mating the first duplication plate 300 and the second duplication plate 301. The second duplication plate 301 has an inverted shape of the needle-shaped body main body 10 of the needle-shaped body 101 to be produced. The second duplication plate 301 has recess that correspond to the shapes of the needles 12 of the needle-shaped body 101 to be produced. The second duplication plate 301 is also called an intaglio plate or a mold.

A step shown in (c) of FIG. 9 is a step of forming the needle-shaped body 101 by ejecting the thermoplastic resin 4 into a space formed by the first duplication plate 300 and the second duplication plate 301. The thermoplastic resin 4 is integrally formed with the support member 5 on the support member 5. The thermoplastic resin 4 becomes the needle-shaped body main body 10 by the first duplication plate 300 and the second duplication plate 301.

A step shown in (d) of FIG. 9 is a step of removing the needle-shaped body main body 10 and the support member 5 which are integrally formed from the first duplication plate 300 and the second duplication plate 301. According to this step, the needle-shaped body 101 is removed from the first duplication plate 300 and the second duplication plate 301.

Next, another method for producing the needle-shaped body 101 will be described.

The needle-shaped body 101 can be produced by the steps (a) to (f) of FIG. 3 described in the method for producing the needle-shaped body 1 of the first embodiment.

In other words, the method for producing the needle-shaped body 101 includes a step of preparing the prototype 2 for producing the needle-shaped body 1. The method for producing the needle-shaped body 101 includes a step of producing the duplication plate 3. The method for producing the needle-shaped body 101 includes a step of removing the prototype 2 from the duplication plate 3. The method for producing the needle-shaped body 101 includes a step of filling the thermoplastic resin 4 into the duplication plate 3 to form the needle-shaped body main body 10 which corresponds to the needle-shaped body 1. The method for producing the needle-shaped body 101 includes a step of placing the support member 5 on the second surface 112 of the needle-shaped body main body 10. The method for producing the needle-shaped body 101 includes a step of removing the needle-shaped body main body 10 and the support member 5 which are integrally formed from the duplication plate 3.

According to the fifth embodiment, the needle-shaped body 1 and the method for producing the needle-shaped body 1 can achieve the same effects as those described in the first to fourth embodiments.

The method for producing the needle-shaped body will be described by using specific examples. As a matter of course, the method for producing the needle-shaped body is not limited to examples described below, and other production methods that would occur to a person having ordinary skill in the art are contemplated.

Example 1

The shape of the needle-shaped body 1 produced in Example 1 will be described. The needle-shaped body 1 was made of PGA. The needle 12 had a height of 800 μm. A bottom length of the needle 12 was 300 μm. Sixteen needles 12 were arranged in 4×4 regular grid pattern. A pitch between the needles 12 was 800 μm. The outer shape of the substrate 11 was a 5 mm square. The substrate 11 had a thickness of 100 μm.

Referring back to FIG. 3, a specific method for producing the needle-shaped body 1 according to the first embodiment will be described.

In the step shown in (a) of FIG. 3, the prototype 2 produced by using a five-axis processing center was prepared. Silicon was used as a material for the prototype 2.

In the step shown in (b) of FIG. 3, Ni electrocasting was performed to the prototype 2 to produce the duplication plate 3.

In the step shown in (c) of FIG. 3, the prototype 2 made of silicon was removed from the duplication plate 3 by using a hot alkali solution.

By the aforementioned steps, the duplication plate 3 serving as a mold of the needle-shaped body 1 to be produced was prepared. The duplication plate 3 was a Ni plate formed by electrocasting, which was left after the silicon was removed.

In the step shown in (d) of FIG. 3, one of medical grade biocompatible resins, PGA, was filled into the duplication plate 3 to thereby form the needle-shaped body 1. Specifically, PGA was placed on the duplication plate 3. At this point, the amount of PGA filled into the duplication plate 3 was adjusted so that the substrate 11 had the intended thickness. Then, PGA placed on the duplication plate 3 was heated at 250° C. and melted.

Then, pressure was applied to PGA from the above by using a roller made of a silicone rubber to thereby push the PGA into the recesses 32 of the duplication plate 3.

In the step shown in (e) of FIG. 3, a sheet made of PVA was placed on the melted PGA. The sheet made of PVA had the thickness of 400 μm. This PVA sheet constituted the support member 5. Then, pressure was applied to a rear surface of the PVA sheet (the surface that is not in contact with PGA) by using a roller made of a silicone rubber.

In the step shown in (f) of FIG. 3, the duplication plate 3 was cooled from both surfaces. After the temperature of the duplication plate 3 was decreased to around room temperature, vacuum tweezers were applied to the rear surface of the PVA sheet for peeling off in a direction perpendicular to the duplication plate 3. As a result, the needle-shaped body 1 having the substrate 11 and the needles 12 made of PGA and the PVA sheet adhered to the second surface 112 of the substrate 11 were obtained as a unit.

In the step shown in (g) of FIG. 3, when the entire needle-shaped body 1 having the integrally formed PVA sheet was immersed in 25° C. distilled water for five minutes, the PVA sheet was completely dissolved. As a result, the above-mentioned needle-shaped body 1 having sixteen needles 12 standing on the substrate 11 of 100 µm thickness, the needle 12 having 800 µm height and 300 µm bottom length, was obtained.

Example 2

Referring back to FIG. 6, a specific method for producing the needle-shaped body 1 according to the second embodiment will be described.

In Example 2, the embossed structures 511 were formed on one surface of the support member 5.

By the steps (a) to (c) of FIG. 6, the duplication plate 3 serving as a mold of the needle-shaped body 1 to be produced as with Example 1 was produced.

In the step shown in (d) of FIG. 6, one of medical grade biocompatible resins, PGA, was filled into the duplication plate 3 to thereby form the needle-shaped body 1. Specifically, PGA was placed on the duplication plate 3. At this point, the amount of PGA filled into the duplication plate 3 was adjusted so that the substrate 11 had the intended thickness. Then, PGA placed on the duplication plate 3 was heated at 250° C. and melted. Then, pressure was applied to PGA from the above by using a roller made of a silicone rubber to thereby push the PGA into the recesses 32 of the duplication plate 3.

In the step shown in (e) of FIG. 6, a sheet made of PVA was placed on the melted PGA. The embossed structures 511 with the radius of 5 µm were formed on one surface (the surface that is in contact with PGA) of the PVA sheet. The PVA sheet had the thickness of 400 µm. Then, pressure was applied to a rear surface of the PVA sheet (the surface that is not in contact with PGA) by using a roller made of a silicone rubber.

In the step show in (f) of FIG. 6, the duplication plate 3 was cooled from both surfaces. After the temperature of the duplication plate 3 was decreased to around room temperature, vacuum tweezers were applied to the rear surface of the PVA sheet for peeling off in a direction perpendicular to the duplication plate 3. As a result, the needle-shaped body 1 having the substrate 11 and the needles 12 made of PGA and the PVA sheet adhered to the second surface 112 of the substrate 11 were obtained as a unit. On the second surface 112 of the substrate 11, the dimple structures 112a which correspond to the shapes of the embossed structures 511 of the PVA sheet were formed.

In the step shown in (g) of FIG. 6, when the entire needle-shaped body 1 having the integrally formed PVA sheet was immersed in 25° C. distilled water for five minutes, the PVA sheet was completely dissolved. As a result, the above-mentioned needle-shaped body 1 having sixteen needles 12 standing on the substrate 11 of 100 µm thickness, the needle 12 having 800 µm height and 300 µm bottom length, was obtained.

In the step shown in (f) of FIG. 6, the needle-shaped body 1 made of PGA was adhered to the reinforcement layer 6 made of a stainless steel (for example, SUS304) with the curvature of 50 mm. As a result, the needle-shaped body 1 having sixteen needles 12 standing on the substrate 11 having the curvature of 50 mm, the needle 12 having 800 µm height and 300 µm bottom length, was obtained.

Example 3

A specific method for producing the needle-shaped body 101 according to the fifth embodiment will be described.

The shape of the needle-shaped body 101 produced in Example 5 which is shown in FIG. 7 will be described. The needle 12 of the needle-shaped body 101 had the same shape as the needle 12 of Example 1. The height of the needle 12 was 800 µm and the bottom length was 300 µm. Sixteen needles 12 were arranged in 4×4 regular grid pattern. A pitch between the needles 12 was 800 µm. The outer shape of the substrate 11 was a 5-mm square. The substrate 11 had a thickness of 100 µm.

Referring back to FIG. 3, a specific method for producing the needle-shaped body 1 according to the fifth embodiment will be described.

In the step shown in (a) of FIG. 3, the prototype 2 produced by using a five-axis processing center was prepared. Silicon was used as a material for the prototype 2.

In the step shown in (b) of FIG. 3, Ni electrocasting was performed to the prototype 2 to produce the duplication plate 3.

In the step shown in (c) of FIG. 3, the prototype 2 made of silicon was removed from the duplication plate 3 by using a hot alkali solution.

By the aforementioned steps, the duplication plate 3 serving as a mold of the needle-shaped body 1 to be produced was prepared. The duplication plate 3 was a Ni plate formed by electrocasting, which was left after the silicon was removed.

In the step shown in (d) of FIG. 3, one of medical grade biocompatible resins, PGA, was filled into the duplication plate 3 to thereby form the needle-shaped body. Specifically, PGA was placed on the duplication plate 3. At this point, the amount of PGA filled into the duplication plate 3 was adjusted so that the substrate 11 had the intended thickness. Then, PGA placed on the duplication plate 3 was heated at 250° C. and melted. Then, pressure was applied to the PGA from the above by using a roller made of a silicone rubber to thereby push the PGA into the recesses 32 of the duplication plate 3.

In the step shown in (e) of FIG. 3, a sheet made of general grade PGA which is non-biocompatible was placed on the melted PGA. The PVA sheet had the thickness of 400 µm, and was less expensive than the medical grade raw PGA which was used for the needle-shaped body. This PGA sheet constitutes the support member 5. Then, pressure was applied to a rear surface of the PGA sheet by using a roller made of a silicone rubber.

In the step show in (f) of FIG. 3, the duplication plate 3 was cooled from both surfaces. After the temperature of the duplication plate 3 was decreased to around room temperature, vacuum tweezers were applied to the rear surface of the PVA sheet for peeling off in a direction perpendicular to the duplication plate 3. As a result, the needle-shaped body 1 having the substrate 11 and the needles 12 made of PGA and the PGA sheet adhered to the second surface 112 of the substrate 11 were obtained as a unit. Thus, the needle-shaped body 101 shown in FIG. 7 was obtained.

The present invention is not limited to the aforementioned embodiments, and various modifications can be made in the implementation stages without departing from the spirit of the invention. Further, inventions in various stages are included in the above embodiments, and various inventions can be extracted by appropriately combining a plurality of constituent elements disclosed.

For example, even if some constituent elements are eliminated from all the constituent elements disclosed in the embodiments, the configuration with these constituent elements eliminated can be extracted as the invention as long as the problem described in the section of the technical problem can be solved and the effect describe in the section of the advantageous effects of invention can be achieved.

REFERENCE SIGNS LIST

1 . . . Needle-shaped body, 2 . . . Prototype, 3 . . . Duplication plate, 4 . . . Thermoplastic resin, 5 . . . Support member, 6 . . . Reinforcement layer, 7 . . . Adhesive layer, 10 . . . Needle-shaped body main body, 11 . . . Substrate of needle-shaped body, 12 . . . Needle of needle-shaped body, 21 . . . Substrate of prototype, 22 . . . Needle of prototype, 31 . . . First surface of duplication plate, 32 . . . Recess of duplication plate, 51 . . . Surface of support member, 61 . . . Curved surface, 101 . . . Needle-shaped body, 111 . . . First surface (needle forming surface) of needle-shaped body, 112 . . . Second surface (non-needle forming surface) of needle-shaped body, 112a . . . Recess (dimple structure), 112b . . . Projection (embossed structure), 112c . . . Projection (embossed structure), 211 . . . First surface of prototype, 212 . . . Second surface of prototype, 511 . . . Projection (embossed structure) of support member, 300 . . . First duplication plate, 301 . . . Second duplication plate

What is claimed is:

1. A method for producing a needle-shaped body, the method comprising the steps of:
    filling a melted thermoplastic resin into a duplication plate having recesses having inverted needle shapes;
    applying a support member to a surface of the thermoplastic resin, which is opposite to a surface of the thermoplastic resin facing the duplication plate, wherein the support member is made of a material different from the thermoplastic resin of;
    removing the thermoplastic resin and the support member, which are integrally formed on the duplication plate, from the duplication plate; and
    removing the support member from the thermoplastic resin using a solvent in which the material for the support member is soluble, wherein the removed thermoplastic resin forms a needle-shaped body comprising a substrate having a first surface having needles.

2. The method for producing a needle-shaped body of claim 1, wherein the support member is made of a water-soluble material.

3. The method for producing a needle-shaped body of claim 1, wherein the support member is made of polyvinyl alcohol.

4. The method for producing a needle-shaped body of claim 1, wherein a surface of the support member that is in contact with the thermoplastic resin has a recess, a projection or a configuration made by combination thereof.

5. The method for producing a needle-shaped body of claim 1, further comprising a step of adhering, after the support member has been removed, the surface of the thermoplastic resin that faced the support member, to a convex curved surface of a reinforcement layer.

6. A method for producing a needle-shaped body having needles on a first surface of a substrate made of a thermoplastic resin, the method comprising the steps of:
    forming the needle-shaped body by filling the thermoplastic resin into a duplication plate having recesses that correspond to shapes of the needles;
    providing a support member made of a material different from a material for the needle-shaped body on a second surface of the substrate which is opposite to the first surface;
    removing the needle-shaped body and the support member which are integrally formed from the duplication plate;
    removing the support member from the needle-shaped body; and
    adhering the second surface of the substrate, with the support member removed, to a convex curved surface of a reinforcement layer.

7. The method for producing a needle-shaped body of claim 6, wherein the support member is made of a water-soluble material.

8. The method for producing a needle-shaped body of claim 6, wherein the support member is made of polyvinyl alcohol.

9. The method for producing a needle-shaped body of claim 6, wherein a surface of the support member that is in contact with the second surface of the substrate has a recess, a projection or a configuration made by combination thereof.

10. A method for producing a needle-shaped body, the method comprising the steps of:
    filling a melted thermoplastic resin into a duplication plate having recesses having inverted needle shapes;
    applying a support member to a surface of the thermoplastic resin, which is opposite to a surface of the thermoplastic resin facing the duplication plate, wherein the support member is made of a material different from the thermoplastic resin;
    removing the thermoplastic resin and the support member, which are integrally formed on the duplication plate, from the duplication plate; and
    removing the support member from the thermoplastic resin, wherein the removed thermoplastic resin forms a needle-shaped body comprising a substrate having a first surface having needles,
    wherein the step of applying the support member is a step of adhering the support member to the thermoplastic resin by using an adhesive having adhesiveness that varies in response to external stimulation or wherein the material of the support member has adhesiveness that varies in response to external stimulation to the thermoplastic material and
    the step of removing the support member from the thermoplastic material comprises applying the external stimulation.

11. The method for producing a needle-shaped body of claim 10, wherein the support member is made of a water-soluble material.

12. The method for producing a needle-shaped body of claim 10, wherein the support member is made of polyvinyl alcohol.

13. The method for producing a needle-shaped body of claim 10, wherein the external stimulation is ultraviolet light, electron beam, infrared light or heat.

14. The method for producing a needle-shaped body of claim 10, wherein a surface of the support member that is in contact with the thermoplastic resin has a recess, a projection or a configuration made by combination thereof.

* * * * *